United States Patent
Fukutani (10) Patent No.: US 8,942,058 B2
(45) Date of Patent: Jan. 27, 2015

(54) DISPLAY DATA OBTAINING APPARATUS AND DISPLAY DATA OBTAINING METHOD

(75) Inventor: Kazuhiko Fukutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 723 days.

(21) Appl. No.: 13/074,161

(22) Filed: Mar. 29, 2011

(65) Prior Publication Data

US 2011/0261056 A1   Oct. 27, 2011

(30) Foreign Application Priority Data

Apr. 27, 2010 (JP) ................. 2010-101886
Mar. 8, 2011 (JP) ................. 2011-050008

(51) Int. Cl.
- *G01S 15/00* (2006.01)
- *A61B 5/00* (2006.01)
- *A61B 8/00* (2006.01)

(52) U.S. Cl.
CPC ............. *A61B 5/0073* (2013.01); *A61B 5/0095* (2013.01); *A61B 8/00* (2013.01)
USPC .......................................................... 367/7

(58) Field of Classification Search
USPC .......................................................... 367/7
See application file for complete search history.

(56) References Cited

U.S. PATENT DOCUMENTS

| 7,864,307 B2 | 1/2011 | Fukutani et al. ............ 356/73 |
| 2005/0288592 A1* | 12/2005 | Yamamoto .................. 600/473 |
| 2008/0306371 A1 | 12/2008 | Fukutani et al. ............ 600/407 |
| 2009/0069685 A1 | 3/2009 | Nishihara et al. .......... 600/443 |
| 2009/0198128 A1 | 8/2009 | Fukutani et al. ............ 600/437 |
| 2010/0049049 A1 | 2/2010 | Asao et al. .................. 600/433 |
| 2010/0053618 A1 | 3/2010 | Nakajima et al. ........... 356/432 |
| 2010/0087733 A1 | 4/2010 | Nakajima et al. ........... 600/437 |

(Continued)

FOREIGN PATENT DOCUMENTS

| CN | 1846645 | 10/2006 |
| CN | 101669816 | 3/2010 |

(Continued)

OTHER PUBLICATIONS

Office Action issued Dec. 13, 2012 in counter PR China application 201110101353.7, with translation.

(Continued)

*Primary Examiner* — Isam Alsomiri
*Assistant Examiner* — James Hulka
(74) *Attorney, Agent, or Firm* — Fitzpatrick, Cella, Harper & Scinto (57) ABSTRACT

Provided is a display data obtaining apparatus capable of, in photoacoustic tomography, reducing a fluctuation in sensitivity which depends on location for image reconstruction even in a limited measurement condition in which a photoacoustic wave generated in the entire subject cannot be obtained in a sufficient range. The display data obtaining apparatus includes: an acoustic wave detecting unit for detecting an acoustic wave generated from a subject irradiated with pulsed light to obtain a signal; a first data deriving unit for deriving first data exhibiting an optical characteristic distribution of the subject based on the obtained signal obtained by the acoustic wave detecting unit; a memory for storing spatial sensitivity distribution data specific to the display data obtaining apparatus; and a second data deriving unit for deriving second data exhibiting the optical characteristic distribution of the subject using the first data and the spatial sensitivity distribution data.

20 Claims, 5 Drawing Sheets

(56) References Cited

U.S. PATENT DOCUMENTS

| | | | |
|---|---|---|---|
| 2010/0174197 A1 | 7/2010 | Nakajima et al. | 600/478 |
| 2010/0191109 A1 | 7/2010 | Fukutani et al. | 600/437 |
| 2010/0331662 A1 | 12/2010 | Fukutani et al. | 600/407 |
| 2011/0128816 A1 | 6/2011 | Baba et al. | 367/11 |
| 2001/0194380 | 8/2011 | Fukuktani | 367/140 |

FOREIGN PATENT DOCUMENTS

| | | |
|---|---|---|
| JP | 2009-066110 | 4/2009 |
| WO | 2009/154298 | 12/2009 |

OTHER PUBLICATIONS

S.A. Ermilov et al., "128-Channel Laser Optoacoustic Imaging System (LOIS-128) for Breast Cancer Diagnostics", *Proceedings of SPIE*, vol. 6086, pp. 608609-1 through 608609-12 (2006).

M. Xu et al., "Photoacoustic Imaging in Biomedicine", *Review of Scientific Instruments*, vol. 77, pp. 041101-1 through 041101-22 (2006).

\* cited by examiner

DISPLAY DATA OBTAINING APPARATUS AND DISPLAY DATA OBTAINING METHOD

BACKGROUND OF THE INVENTION

1. Field of the Invention

The present invention relates to a display data obtaining apparatus and a display data obtaining method with which a signal of an acoustic wave from an inner portion of a subject to be examined (hereinafter, referred to as "subject") irradiated with light is detected, and the detected signal is processed to obtain information of the inner portion of the subject.

2. Description of the Related Art

In medical fields, there has been actively developed an optical imaging apparatus for irradiating a living body with light emitted from a light source such as a laser, and for displaying on a display information of an inner portion of the living body which is obtained based on light entering the living body. An example of the optical imaging technology is photoacoustic tomography (PAT). In the photoacoustic tomography, a living body is irradiated with pulsed light from the light source so as to detect an acoustic wave (typically ultrasound) generated from a living tissue having absorbed the energy of the pulsed light being propagated and diffused in the inner portion of the living body. That is, an elastic wave, which is generated when the examined region having absorbed the energy of the irradiated light is momentarily expanded, is received as a detected signal by an acoustic wave detector (also called a probe or transducer) using a difference in an optical energy absorption factor between an examined region (for example, tumor) and the other tissue. When the detected signal is analyzed and processed, an optical characteristic distribution, in particular, an initial sound pressure distribution or absorption coefficient distribution of the inner portion of the living body may be obtained. When the measurement described above is performed with light beams having various wavelengths, the obtained information may also be used to quantitatively measure specific substances in the inner portion of the living subject, for example, a concentration of hemoglobin contained in blood and an oxygen saturation of blood.

There has been known a problem in that, the photoacoustic tomography apparatus causes a spatial sensitivity distribution specific to the apparatus, when an acoustic wave measurement region is insufficient compared to an information acquisition region, for example, when the acoustic wave may be received from not in all directions of a subject but in only a specific direction ("128-channel laser optoacoustic imaging system (LOIS-128) for breast cancer diagnostics", Sergey A. Ermilov, Andre Conjusteau, Ketan Mehta, Ron Lacewell, P. Mark Henrichs, and Alexander A. Oraevsky, Proceedings of SPIE, Vol. 6086, 608609, 2006). A spatial sensitivity distribution is a distribution that exhibits fluctuations in measurement sensitivities for respective locations (sound source positions) in a measurement object. The fluctuation in sensitivities, which depend on locations, occurs because an information amount which may be used for each voxel is changed depending on a relative voxel position difference between the acoustic wave detector and a sound source even in a case where completely the same target parameter (for example, initial sound pressure) is measured. Therefore, results obtained by the detection are displayed using contrasts, which are changed depending on the locations in the measurement object. As a result, the quantitativity of obtained information is deteriorated. The relative position between the acoustic wave detector and the sound source is changed for every apparatus, and hence a spatial sensitivity distribution contrast difference is also changed, respectively. In order to solve the problem described above, it is known that it is important to detect an acoustic wave in all directions of 360° around the subject to obtain a sufficient information amount ("Photoacoustic Imaging in biomedicine", M. Xu and L. V. Wang, Review of Scientific Instruments, 77, 041101, 2006).

However, when a large object, for example, breasts of a human are subjected to examination, it is difficult to measure an acoustic wave in various positions around the entire subject, and hence inner information of a living body cannot be obtained by using a sufficient amount of information. In other words, when such objects are subjected to examination, the method of Xu et al. is not necessarily practical to eliminate the deterioration of the quantitativity of the obtained information.

SUMMARY OF THE INVENTION

The present invention has been made based on the problem as described above. An object of the present invention is to provide a display data obtaining and diagnosis apparatus capable of reducing a fluctuation in sensitivity (spatial sensitivity distribution) for each location in a measurement object even in a limited measurement condition in which a photoacoustic wave generated in the entire subject cannot be obtained in a sufficient range.

In view of the above-mentioned problem, a display data obtaining apparatus according to the present invention includes: an acoustic wave detecting unit for detecting an acoustic wave generated from a subject irradiated with pulsed light to obtain a signal; and a display data obtaining unit for obtaining a display data showing an optical characteristic distribution based on the signal obtained with the acoustic wave detecting unit, in which the display data obtaining unit includes: a first data deriving unit for deriving first data exhibiting an optical characteristic distribution of the subject based on the obtained signal obtained by the acoustic wave detecting unit; a memory for storing spatial sensitivity distribution data specific to the display data obtaining apparatus; and a second data deriving unit for deriving second data exhibiting an optical characteristic distribution of the subject based on the first data and the spatial sensitivity distribution data.

According to the display data obtaining apparatus of the present invention, the fluctuation in sensitivity (spatial sensitivity distribution) which depends on location in the measurement object may be reduced even in the limited measurement condition in which the photoacoustic wave generated in the entire subject cannot be obtained in the sufficient range.

Further features of the present invention will become apparent from the following description of exemplary embodiments with reference to the attached drawings.

DESCRIPTION OF THE EMBODIMENTS

Hereinafter, the present invention is described in more detail with reference to the attached drawings. The same constituent elements are basically denoted by the same reference symbols and the descriptions thereof are omitted.

Hereinafter, an object information obtaining apparatus according to an embodiment of the present invention is described. However, the present invention is not limited to a single apparatus having a configuration described below. The present invention is realized using a method of realizing functions described below, and is also realized by processing of supplying software (computer program) realizing those functions to a system or an apparatus via network or various storage media and allowing the system or a computer (or CPU, MPU, etc.) of the apparatus to read and execute the program.

(Display Data Obtaining Apparatus)

A configuration of the display data obtaining apparatus according to this embodiment is described with reference to FIGS. 1A and 1B. The display data obtaining apparatus according to this embodiment is an apparatus for obtaining subject information (optical characteristic distribution information) of an inner portion of a subject with which apparatus the subject information is obtained and displayed on a display.

With respect to a fundamental hardware configuration, the display data obtaining apparatus according to this embodiment includes a light source 11, an acoustic wave probe 17 serving as an acoustic wave detector (acoustic wave detecting unit), and a display data obtaining unit 19. Pulsed light 12 emitted from the light source 11 is formed into a desired optical distribution shape by an optical system 13 including, for example, a lens, a mirror, an optical fiber, and a diffusion plate, and guided and applied to a subject 15, for example, a living body. When a part of energy of light propagating through an inner portion of the subject 15 is absorbed in an optical absorber 14, for example, a blood vessel (which results in sound source), an acoustic wave 16 (typically ultrasound) is generated by the thermal expansion of the optical absorber 14. The acoustic wave 16 is detected (obtained) by the acoustic wave probe 17 and transferred as information to a signal processing unit 20 including a signal converter 18 and the display data obtaining unit 19. The information of the acoustic wave 16 which is transferred to the signal processing unit 20 is amplified and digitally converted by the signal converter 18, and then converted by the display data obtaining unit 19 into display data with respect to optical characteristic distribution information of the inner portion of the subject. Thus, the display data obtaining apparatus obtains a display data concerning optical characteristic distribution. Then, an image based on the display data is displayed on a display 21.

Note that, the term "display data" is optical characteristic distribution information data converted in a display form of the display 21. The display form of the display 21 is not particularly limited. For example, whether a two-dimensional form or a three-dimensional form is employed may be arbitrarily determined based on a measurement purpose and a configuration of the apparatus. Information which is not required depending on the measurement purpose, for example, brightness information is not necessarily included in the display data.

(Light Source 11)

When the subject is a living body, light with a specific wavelength, which is absorbed in a specific component of constituent components of the living body, is emitted from the light source 11. The light source may be integrally provided in the display data obtaining apparatus according to this embodiment. Alternatively, the light source may be separated and provided as an additional member. The light source is desirably a pulsed light source which may generate pulsed light having a pulse width in a range of the order of several nanoseconds to the order of several hundred nanoseconds. To be specific, in order to efficiently generate the acoustic wave, a pulse width of approximately ten nanoseconds is employed. The light source is desirably a laser because a large output is obtained. A light emitting diode may be used instead of the laser. Examples of the laser which may be used include a solid laser, a gas laser, a dye laser, and a semiconductor laser. An emitting timing, a waveform, and an intensity are controlled by a light source controlling unit (not shown). Note that, the light source controlling unit may be provided with the light source. In the present invention, the wavelength of the used light source is desirably a wavelength at which light propagates to the inner portion of the subject. To be specific, when the subject is a living body, the wavelength is equal to or larger than 500 nm and equal to or smaller than 1,200 nm.

(Optical System 13)

The light 12 emitted from the light source 11 is typically formed into a desired optical distribution shape by optical parts such as a lens and a mirror and guided to the subject. In this case, the light may be propagated through an optical waveguide, for example, an optical fiber, which is used as the entire optical path or a part thereof. The optical system 13 includes, for example, a mirror for reflecting light, a lens for condensing, expanding, and shaping light, a diffusion plate for diffusing light, and an optical fiber. As long as the subject 15 is irradiated with the light 12 emitted from the light source at the desired shape, any optical parts may be used. Note that, in view of the safety of a living body and the effect of expansion of a diagnostic region, the light is desirably expanded to a certain amount of area, rather than condensed by the lens.

(Subject 15 and Optical Absorber 14)

The subject 15 and the optical absorber 14 are not a part of the display data obtaining apparatus according to this embodiment, but are described below. A principal purpose of the display data obtaining apparatus according to this embodiment is the imaging of the inner portion of the living body, particularly, the diagnosis of a malignant tumor or vessel disease of a human or animal and the chemical treatment follow-up thereof. Therefore, the subject 15 which is a diagnostic target region is expected to be a breast, finger, or limb of a living body (specifically, human or animal). In a case of the animal, particularly, in a case of a small animal, for example, a mouse or a rat, not only a specific region but also the entire small animal may be targeted. The optical absorber in the inner portion of the subject has a relatively high absorption coefficient in the subject. Although depending on a wavelength of used light, for example, when a human is a measurement object, the optical absorber 14 corresponds to an oxy-/deoxy-hemoglobin, a blood vessel containing a large amount of oxy-/deoxy-hemoglobin, or a malignant tumor including a large number of neovascular vessels. In the present invention, the term "optical characteristic distribution information" refers to an initial sound pressure distribution in the inner portion of the living body, which is a generation source distribution of an acoustic wave generated by light irradiation, a light energy absorption density distribution and an absorption coefficient distribution which are derived from the initial sound pressure distribution, and a concentration distribution of a constituent component (particularly, oxy-/deoxy-hemoglobin) of a living tissue, which is obtained from the information. For example, an oxygen saturation obtained from a concentration distribution of an oxy-/deoxy-hemoglobin is also included in the "optical characteristic distribution information".

(Acoustic Wave Detecting Unit (Acoustic Wave Probe 17))

The acoustic wave probe 17 serves as the detector for detecting the acoustic wave generated in the surface and inner portion of the subject by the pulsed light, detects (obtains) the acoustic wave, and converts the detected acoustic wave into an electrical signal (obtained signal) which is an analog signal. Hereinafter, the acoustic wave probe 17 may be referred to simply as a probe or a transducer. Any acoustic wave detector capable of detecting an acoustic wave signal, for example, a transducer using a piezoelectric phenomenon, a transducer using light resonance, or a transducer using a change in capacitance may be used. In this embodiment, the acoustic wave probe 17 includes typically multiple receiving elements which are one-dimensionally or two-dimensionally arranged. When such multi-dimensionally arranged elements are used, the acoustic wave may be simultaneously detected at multiple positions, and a measurement time may be shortened. As a result, the influence of vibration of the subject may be reduced.

In the present invention, the acoustic wave probe 17 is provided to be able to receive an acoustic wave from the subject 15 only in a specific direction.

(Signal Converter 18)

The display data obtaining apparatus according to this embodiment desirably includes the signal converter 18 serving as a part of the signal processing unit 20, to amplify the electrical signal obtained from the acoustic wave probe 17 and convert the electrical signal from an analog signal into a digital signal. The signal converter 18 typically includes an amplifier, an A/D converter, and a field programmable gate array (FPGA) chip. When multiple detected signals (obtained signals) are obtained from the acoustic wave probe, the multiple signals may be desirably processed at the same time. In this manner, a time required to display information may be shortened. In this specification, the term "obtained signal" conceptually includes both the analog signal obtained from the acoustic wave probe 17 and the digital signal obtained by the subsequent A/D conversion.

(Display Data Obtaining Unit 19)

The display data obtaining unit 19 principally serves to perform processing described below and convert the digital signal received from the signal converter 18 into display data (first data) associated with optical characteristic distribution of the inner portion of the subject. The display data obtaining unit 19 in the present invention performs correction processing on the first data obtained from the digital signal received from the signal converter 18. The correction processing is a distinguishing feature of the present invention and performed according to a spatial sensitivity distribution specific to the apparatus. As a result, even in a case where a measurement region is limited, the quantitativity of display information may be inhibited from degrading. Note that, the case where the measurement region is limited refers to a state in which an acoustic wave may be received in not all directions around the subject but only in a specific direction as illustrated in FIG. 1A.

The display data obtaining unit 19 includes a computer, for example, a workstation and may perform the formation of the display data and the correction of the formed display data by software in advance programmed. In the present invention, the software used in the workstation includes two modules, that is, a display data forming module 19a for forming the display data (first data deriving unit) and a data correction module 19b for correcting the obtained display data (second data deriving unit). In this invention, the display data forming module 19a and the data correction module 19b are combined to a memory 19c in which the spatial sensitivity distribution data specific to the apparatus is stored, to serve as a single program, and to thereby provide the single display data obtaining unit 19 as illustrated in each of FIGS. 1A and 1B. In a case of photoacoustic tomography, for example, processing for reducing noises of signals received at respective positions is normally performed as preprocessing before the formation of data to be displayed on the display. The processing may be performed by the display data forming module 19a in the present invention. The noise reduction processing and the correction of a sensitivity distribution resulting from a structural or physical property distribution of the subject may be performed independently from the correction of the spatial sensitivity distribution in the present invention.

The display data forming module 19a basically functions to derive the first data by, for example, back projection in time domain or Fourier domain which is normally used in a tomography technology. Note that, when a long time is permitted to be spent in this stage, for example, an iterative reconstruction method of performing repetition processing may be used. As described by Xu et al., examples of typical methods used in the PAT include a Fourier transform method, a universal back projection method, a filtered back projection method, and an iterative reconstruction method. In the present invention, any of the methods may be used.

The data correction module 19b performs various corrections on the first data generated by the display data forming module 19a. In the present invention, particularly, each voxel data of the first data is divided or multiplied by a coefficient based on the spatial sensitivity distribution data specific to the apparatus, which is stored in the memory 19c, to derive second data. In other words, the spatial sensitivity distribution specific to the apparatus is reduced. Note that, the spatial sensitivity distribution data specific to the apparatus may be calculated in advance or calculated depending on apparatus specifications when the first data is derived. When a calculation module 19d for calculating the spatial sensitivity distribution data (calculation unit) is provided in the display data obtaining unit 19 as illustrated in FIG. 1B, the spatial sensitivity distribution data may be calculated at any time. Note that the calculation module 19d may not be provided in the display data obtaining unit 19 and the spatial sensitivity distribution data may be calculated without depending on the display data obtaining apparatus according to the present invention.

In some cases, the signal converter 18 and the display data obtaining unit 19 may be integrally provided. In such cases, the display data of the subject may also be generated not by software processing executed by the workstation but may be by hardware processing.

(Display 21)

The display 21 is a device for displaying the display data output from the display data obtaining unit 19 and typically includes a liquid crystal display. Note that, the display may be provided separate from the display data obtaining apparatus according to the present invention.

Next, an example of spatial sensitivity distribution correction processing which is a distinguishing feature of the present invention is described with reference to FIGS. 2, 3A, 3B, and 3C. The following numbers correspond to processing numbers of FIG. 2.

(Detection of Acoustic Wave)

Processing-0 (S101, 102): Step of Detecting Acoustic Wave, Generated Inside Subject when the Subject is Irradiated with Pulsed Light, with Acoustic Wave Probe 17

When a subject 15 is irradiated with light 12 from light source 11 (S101), acoustic wave 16 is generated due to photoacoustic effect at an optical absorber 14 inside the subject 15. The acoustic wave 16 is detected with acoustic probe 17 (S102), and converted into electric signal by the acoustic probe 17.

(Processing of Obtained Signal)

Figure 3A:
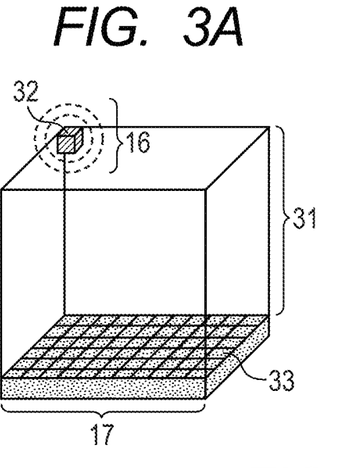
FIG. 3A is a schematic view illustrating an example of a method of calculating data on a spatial sensitivity distribution in the present invention.
Figure 3B:
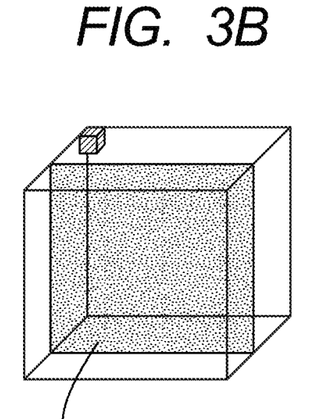
FIG. 3B is a schematic view illustrating the example of the method of calculating the data on the spatial sensitivity distribution in the present invention.
Figure 3C:
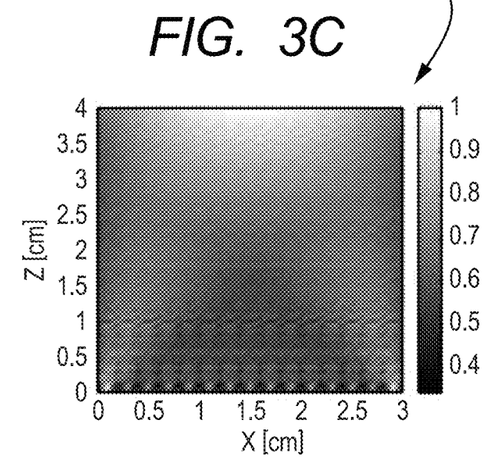
FIG. 3C illustrates an example of the spatial sensitivity distribution obtained by the calculating method in the present invention.

Processing-1 (S201): Step of Calculating Spatial Sensitivity Distribution Data Corresponding to Specifications of Photoacoustic Tomography Apparatus The spatial sensitivity distribution data specific to the apparatus, which corresponds to the hardware configuration of the photoacoustic tomography apparatus and the display data forming method, is calculated. The hardware configuration of the photoacoustic tomography apparatus refers to the number of elements of the acoustic wave probe 17, a scanning region, a detection element size, and a band, and so on, which particularly affect the display data. In the present invention, it is necessary to calculate the spatial sensitivity distribution data suitable for the respective apparatus specifications. Various calculation methods may be used and an example of one of the calculation methods is described hereinafter. FIGS. 3A, 3B, and 3C schematically illustrate an example of the method of calculating the spatial sensitivity distribution data. First, as illustrated in FIG. 3A, a measurement object 31 is divided into multiple voxels 32. Note that, while the example of three-dimensional voxel division is described, the same method may be used for one-dimensional or two-dimensional division. Next, the propagation of an acoustic wave is estimated with the assumption that an arbitrarily determined voxel of the multiple voxels is a primary sound source. An acoustic wave signal from the determined voxel, which is to be received (obtained) by the acoustic wave probe 17 used in the photoacoustic tomography apparatus, is calculated. For example, when the respective voxels are assumed to be spherical sound sources in which light is uniformly absorbed and an analytical solution is used, received (obtained) signals may be easily calculated. Note that, in this case, characteristics of the probe for receiving the signals, for example, a detection element size 33 and a receiving band are desirably taken into account.

Next, as illustrated in FIG. 3B, a measurement sensitivity of a voxel corresponding to a position of the sound source generating the sound wave is calculated based on the calculated received signal (obtained signal) of the acoustic wave. For example, even in a case of an apparatus for forming display data by a universal back projection method (see Xu et al.) which is one of time domain methods, the same method is desirably used to calculate the measurement sensitivity value of the voxel corresponding to the position of the sound source. When such processing is performed on all the spatial voxels, the spatial sensitivity distribution data specific to the apparatus is obtained.

FIG. 3C illustrates a two-dimensional tomographic image (shaded part of FIG. 3B) clipped from the calculated spatial sensitivity distribution data. As is apparent from FIG. 3C, the sensitivity varies depending on positions.

Figure 5:
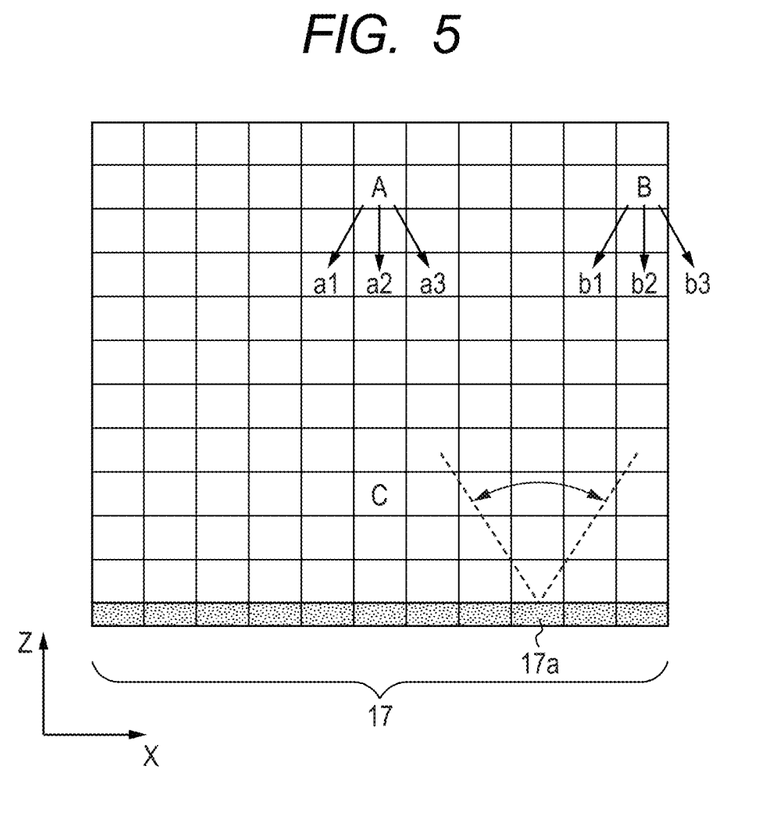
FIG. 5 is a schematic view qualitatively illustrating the spatial sensitivity distribution.

FIG. 5 is an explanatory view illustrating that the sensitivity varies depending on positions, and illustrates divided voxels corresponding to FIG. 3C (shaded part of FIG. 3B). A shaded part in FIG. 5 corresponds to an acoustic wave probe array. Arbitrary selected voxels are expressed by "A", "B", and "C". Directions from the voxel "A" are expressed by a1, a2, and a3. Directions from the voxel "B" are expressed by b1, b2, and b3, and are the same as the directions a1, a2, and a3, respectively.

As illustrated in FIG. 3C, the sensitivity is not the same between the voxel "A" and the voxel "B". The reason is as follows. Of acoustic waves generated from the voxel "A" illustrated in FIG. 5, acoustic waves propagating in the respective directions a1, a2, and a3 all travel toward the acoustic wave probe 17 and are to be detected by an element of the acoustic wave probe 17. On the other hand, of acoustic waves generated from the voxel "B", while acoustic waves propagating in the directions b1 and b2 travel toward the acoustic wave probe 17, an acoustic wave propagating in the direction b3 travels toward a region in which the acoustic wave probe 17 is not provided, and is not obtained by the acoustic wave probe 17. Therefore, the detecting range of acoustic waves used for image reconstruction in the display data obtaining unit 19 is changed between the voxel "A" and the voxel "B". In other words, the number of elements of the acoustic wave probe 17 used for image reconstruction in the display data obtaining unit 19 is changed between the voxel "A" and the voxel "B". Thus, the spatial sensitivity of voxel in an X-direction is changed. Note that, even when the acoustic wave probe array is used for scanning in the X-direction, the spatial sensitivity is changed between an end part of a scanning region and a central part of the scanning region.

As illustrated in FIG. 3C, the sensitivity is also changed between the voxel "A" and the voxel "C". The reason is that the number of elements of the acoustic wave probe 17 used for image reconstruction in the display data obtaining unit 19 is changed between the voxel "A" and the voxel "C". To be specific, the acoustic wave probe 17 is finite in size, and has the directivity of detection sensitivity in which acoustic waves may be highly detected in directions within an angle range between broken lines of FIG. 5. Therefore, an acoustic wave probe element 17a has high detection sensitivity for acoustic waves generated from the voxel "A" but low detection sensitivity for acoustic waves generated from the voxel "C". Thus, the acoustic wave probe element 17a may be used for image reconstruction of the voxel "A" but cannot be used for image reconstruction of the voxel "C", and hence the number of elements of the acoustic wave probe 17 used for image reconstruction is changed between the voxel "A" and the voxel "C". Therefore, even in a Z-direction, the spatial sensitivity of voxel is changed.

Note that, the calculation processing as described above may be performed at any time if the configuration of the apparatus and the method used to derive the first data are determined. Therefore, in order to reduce a total processing time, the calculation may be performed in advance before measurement. In this case, as is apparent from the signal processing unit 20 illustrated in FIG. 1A, it is unnecessary to incorporate the calculation module for calculating the spatial sensitivity distribution data into the apparatus. Note that, when the configuration of the apparatus and the method used to derive the first data are changed as appropriate, the calculation may be performed after signals are received by the signal converter 18. In this case, as illustrated in FIG. 1B, the calculation module 19d for calculating the spatial sensitivity distribution data is required.

The example in which the spatial sensitivity distribution data is obtained by calculation is described herein. However, the method of calculating the spatial sensitivity distribution data is not limited to this. For example, a small-size sound source may be actually provided in the position corresponding to each of the voxels, acoustic waves generated from the corresponding voxel are received, and the sensitivity data in the position of the sound source may be calculated based on the received signals. Such processing may be repeated in various positions to experimentally calculate the spatial sensitivity distribution data.

Processing-2 (S202): Step of Storing Spatial Sensitivity Distribution Data Calculated in Processing-1 into Memory When the signal processing unit 20 is a computer such as a workstation, the spatial sensitivity distribution data calculated by the processing described above is saved in a file of a hard disk (not shown), and stored in the memory 19c of the workstation when the data is used. Alternatively, the result is stored in the memory 19c simultaneously with the calculation. In this step, any method may be used as long as the spatial sensitivity distribution data can be stored in the memory 19c.

Processing-3 (S203): Step of Deriving First Data Associated with Optical Characteristic Distribution of Subject Based on Received Signals Obtained by Signal Converter 18

In this step, first data associated with optical characteristic distribution information including an initial sound pressure distribution of acoustic waves generated from the subject 15 irradiated with light is derived from, for example, the digital signal obtained from the signal converter 18. In order to form the optical characteristic distribution, any processing method used for photoacoustic tomography may be used. For example, in order to form the initial sound pressure distribution, back projection in time domain or Fourier domain may be employed. Note that, this processing method is desirably the same as the method used to calculate the spatial sensitivity distribution data. When the same method is used, the sensitivity distribution may be accurately corrected in Processing-4 described later. For example, when a universal back projection method which is one of time domain methods is employed to calculate the spatial sensitivity distribution data as described in the calculation example, the initial sound pressure distribution is formed by the following expressions.

Ex. 1

$$p_0(r) = \int_{\Omega_0} b(r_0, t = |r - r_0|) \frac{d\Omega_0}{\Omega_0} \quad (1)$$

where $P_0(r)$ indicates the initial sound pressure distribution, $b(r_0,t)$ indicates projection data, and $d\Omega_0$ indicates a solid angle of a detector $dS_0$ relative to an arbitrary observation point P. When the projection data is back-projected by the integration of Expression (1), the initial sound pressure distribution $P_0(r)$ may be obtained.

Note that, $b(r_0,t)$ and $d\Omega_0$ are expressed as follows.

Ex. 2

$$b(r_0, t) = 2p(r_0, t) - 2t \frac{\partial p(r_0, t)}{\partial t} \quad (2)$$

Ex. 3

$$d\Omega_0 = \frac{dS_0}{|r - r_0|^2} \cos\theta \quad (3)$$

where $\theta$ indicates an angle formed between the detector and the arbitrary observation point P.

After that, the absorption coefficient distribution or the oxygen saturation may be calculated based on the obtained initial sound pressure distribution.

The optical characteristic distribution information obtained by the step described above is assumed as the first data.

Processing-4 (S204): Step of Deriving Second Data Using First Data Obtained in Processing-3 and Spatial Sensitivity Distribution Data Stored in Memory in Processing-2

For example, each voxel data of the first data obtained in Processing-3 is multiplied or divided by the spatial sensitivity distribution data to correct each voxel value, to thereby derive the second data exhibiting the optical characteristic distribution. In this manner, an effect of the spatial sensitivity distribution dependent on the apparatus may be reduced to improve the quantitativity. Note that, when the number of voxels of the first data obtained in Processing-3 is different from the number of voxels of the spatial sensitivity distribution data, the number of voxels and the positions thereof are adjusted by data interpolation. All the voxels are not necessarily corrected. For example, when a position of a sound source is identified in advance, only a voxel located in the position of the sound source needs to be corrected. In this manner, a calculation time may be shortened.

Figure 1A:
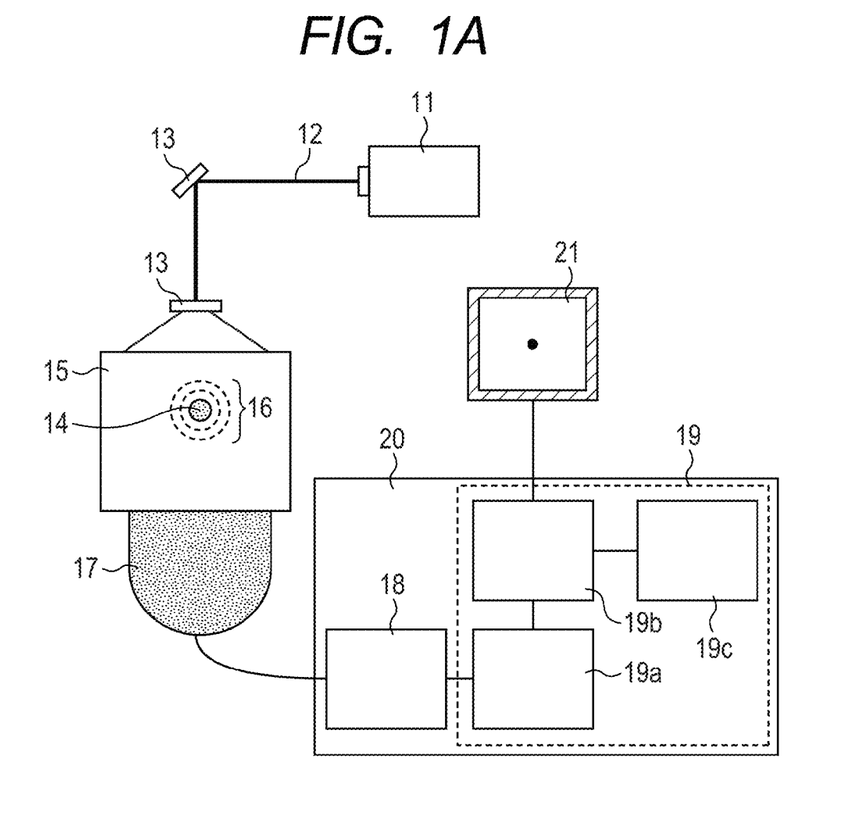
FIG. 1A is a schematic diagram illustrating a configuration of a display data obtaining apparatus according to an embodiment of the present invention.

In the case where the steps described above are executed, even when the acoustic wave receiving range is limited as the example illustrated in FIG. 1A, the spatial sensitivity distribution may be reduced to provide display data with less degradation in quantitativity.

Processing-5 (S301): Step of Displaying Second Data Obtained in Processing-4 signal processing unit 20 displays an image based on the second data on display 21

EXAMPLES

Example 1

Figures 4A, 4B:
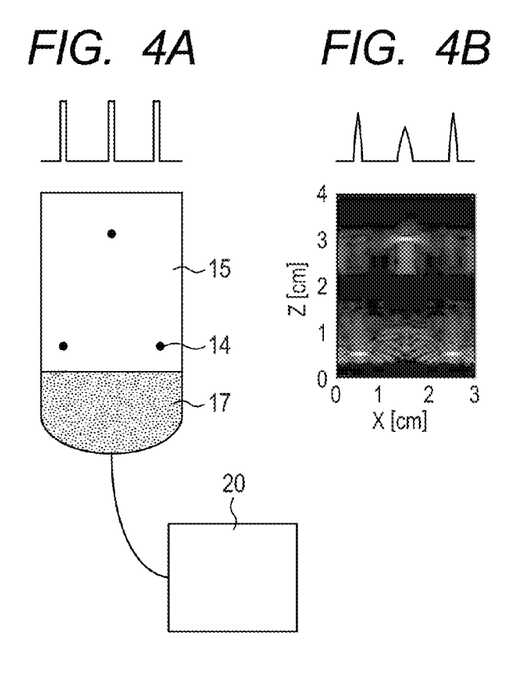
FIG. 4A is a schematic view illustrating a measurement object that was used in Example 1.
FIG. 4B illustrates first data before correction, which was obtained in Example 1.

An example of the display data obtaining apparatus using a photoacoustic tomography, to which the embodiment of the present invention is applied, is described. The display data obtaining apparatus is described with reference to the schematic diagrams of FIGS. 1A and 1B. In this example, a Q-switch YAG laser for generating pulsed light of approximately 10 nanoseconds at a wavelength of 1,064 nm was used as the light source 11. The energy of the pulsed light generated from the laser is 0.6 J. The optical system 13 including a mirror and a beam expander was set so that the pulsed light was expanded to a radius of approximately 2 cm by the optical system 13 to irradiate the subject opposed to the acoustic wave probe 17 with the pulsed light. A rectangular phantom simulating a living body as illustrated in FIG. 4A was used as the subject 15. The used phantom was obtained by solidifying water with agar. The phantom was 5 cm in width, 5 cm in height, and 4 cm in depth. As illustrated in FIG. 4A, three substances which are solidified into a spherical shape with a diameter of 1 mm and colored with ink is each buried as the optical absorber 14 in the phantom. Note that, absorption coefficient values of each of the optical absorbers 14 were adjusted to be equal to one another. Plots illustrated in FIG. 4A exhibit the absorption coefficient values at respective positions.

For acoustic matching, the phantom and the acoustic wave probe were set in a water bath filled with degassed water. As illustrated in FIG. 1A, the phantom set as described above was irradiated with the pulsed light 12 from a phantom surface side opposed to the acoustic wave probe 17. Note that, the used acoustic wave probe 17 was an ultrasonic transducer made of lead zirconate titanate (PZT). The ultrasonic transducer is of a two-dimensional array type. The number of elements is 345 (15×23). An element pitch is 2 mm. An element width is approximately 2 mm.

As illustrated in FIG. 1A, when the pulsed light 12 is applied to the surface of the phantom located under the acoustic wave probe 17, the light is absorbed in the spherical optical absorbers 14 to generate photoacoustic waves. The photoacoustic waves were simultaneously received (detected) in 345 channels by the ultrasonic transducer 17 (acoustic wave probe). Detected signals (obtained signals) were converted into digital data of the photoacoustic waves in all the channels by the signal converter 18 including the amplifier, the A/D converter, and the FPGA. Note that, in order to improve an S/N ratio of the signals, the pulsed light was emitted 30 times from the laser and all detected signals (obtained signals) were averaged. After that, the obtained digital data was transferred to the workstation (WS) as the signal processing unit 20 and stored in the WS. The digital data was used to derive the first data exhibiting the absorption coefficient distribution by the display data forming module 19a. In this case, a universal back projection method as a time domain method was employed to derive three-dimensional volume data. A used voxel interval was set to 0.05 cm. A region for forming the display data was 3.0 cm×4.6 cm×4.0 cm. An example of the first data which was derived as described above is illustrated in FIG. 4B. Note that, FIG. 4B illustrates a two-dimensional tomographic image including all optical absorbers, which is clipped from the three-dimensional first data. Plots illustrated in FIG. 4B schematically exhibit contrasts of the optical absorbers at respective positions.

Figure 1B:
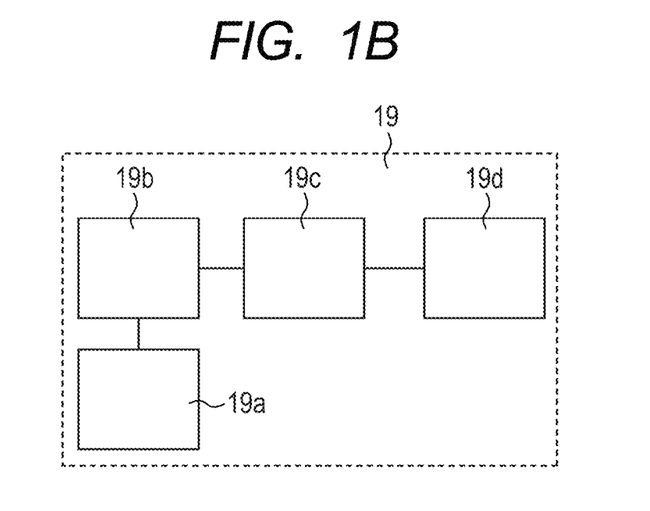
FIG. 1B is a schematic diagram illustrating a structural example of a signal processing unit of the display data obtaining apparatus according to the embodiment of the present invention.
Figure 2:
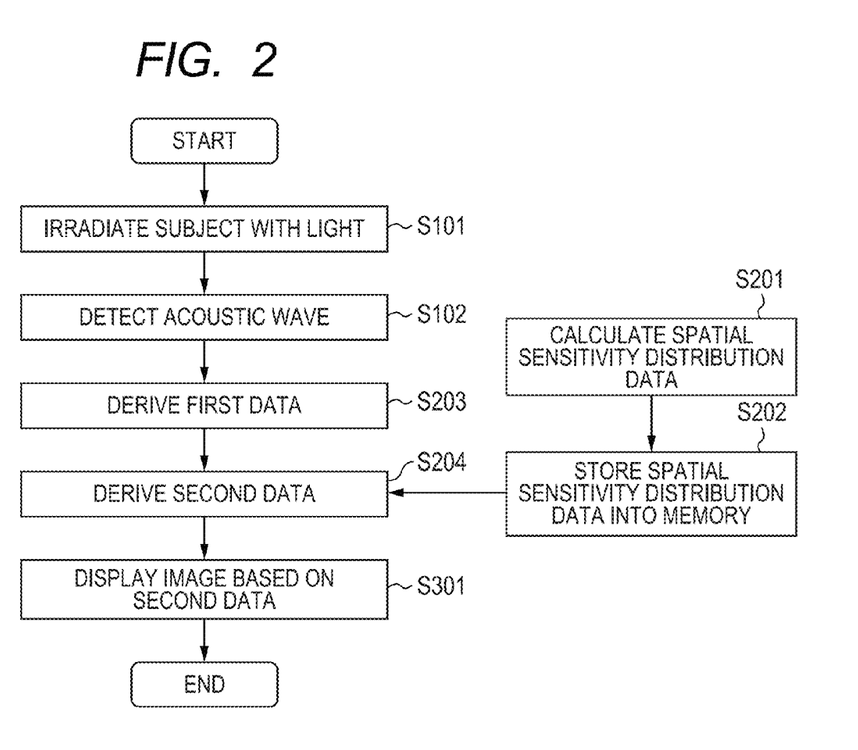
FIG. 2 is a flow chart illustrating an example of detected signal (obtained signal) processing in the embodiment of the present invention.
Figure 4C:
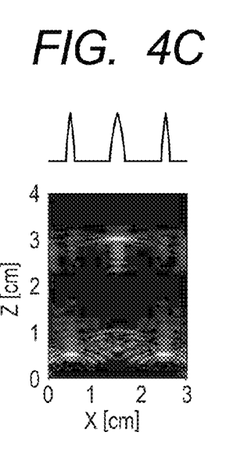
FIG. 4C illustrates second data after correction, which was obtained in Example 1.

Next, the universal back projection method adopted as above was used to calculate spatial sensitivity distribution data of 3.0 cm×4.6 cm×4.0 cm as the same region as described above by the calculation module 19d incorporated in the signal processing unit 20 as illustrated in FIG. 1B. As a result, the spatial sensitivity distribution data illustrated in FIG. 3C was obtained. In this case, in order to avoid the spatial sensitivity distribution data from being divided by zero during the correction, data values of the spatial sensitivity distribution data were normalized with a maximum data value. Further, when a data value was equal to or smaller than 0.5, the data value was set to 1. After that, the spatial sensitivity distribution data was stored in the memory 19c of the workstation as the signal processing unit 20. The first data illustrated in FIG. 4B was divided by spatial sensitivity distribution data in a position corresponding to each voxel of the first data by the data correction module 19b to correct the spatial sensitivity distribution. An example of the second data exhibiting the absorption coefficient distribution which was derived as described above is illustrated in FIG. 4C. FIG. 4C also illustrates a two-dimensional tomographic image including all optical absorbers, which is clipped from the three-dimensional second data. Plots illustrated in FIG. 4C schematically exhibit contrasts of the optical absorbers at respective positions.

FIG. 4B is compared with FIG. 4C. In FIG. 4B, acoustic waves may be received from only a surface of the phantom as in the case of FIG. 1A. Therefore, the absorption coefficients of the respective optical absorbers are equal to one another but the optical absorbers are displayed with different contrasts. In contrast to this, as is apparent from FIG. 4C, the optical absorbers are displayed with substantially the same contrast because of the correction using the spatial sensitivity distribution data. In other words, the quantitativity is significantly improved. As described above, when the first data is corrected using the spatial sensitivity distribution data in the case where the acoustic wave measurement region is limited, the information of the optical absorbers in the inner portion of the subject may be quantitatively displayed.

Example 2

An example of the display data obtaining apparatus using the photoacoustic tomography, to which the embodiment of the present invention is applied, is described. In this example, the same phantom and measurement system as in Example 1 were used. Note that, the first data deriving method and the configuration of the apparatus are known. Therefore, the spatial sensitivity distribution data was calculated in advance by a workstation as a calculation unit prepared separately from the display data obtaining apparatus. After that, the spatial sensitivity distribution data was stored in a hard disk of another workstation as the display data obtaining unit 19 of the display data obtaining apparatus. Note that, the spatial sensitivity distribution data was calculated by substantially the same method as in Example 1.

Next, the phantom is irradiated with light as in Example 1. Obtained digital data was transferred to the workstation (WS) as the signal processing unit 20 and stored in the WS. The digital data was used to derive the first data exhibiting the absorption coefficient distribution as illustrated in FIG. 4B as in Example 1. Then, the spatial sensitivity distribution data stored in the workstation was stored in the memory 19c and the first data was subjected to the spatial sensitivity distribution correction. Unlike Example 1, each voxel of the first data in was multiplied by the spatial sensitivity distribution data in the same position to correct the spatial sensitivity distribution. As a result, second data exhibiting an absorption coefficient distribution with less degradation was able to be derived as in the case of FIG. 4C.

As described above, according to the present invention, even in the case where the spatial sensitivity distribution data is calculated in advance, when the configuration of the apparatus and the first data deriving method are determined, the first data may be corrected to quantitatively display the information of the optical absorbers in the inner portion of the subject.

Example 3

An example of the display data obtaining apparatus using the photoacoustic tomography, to which the embodiment of the present invention is applied, is described. In this example, the same phantom and measurement system as in Example 1 were used. First, before the measurement of the phantom, a very-small optical absorber in which ink entered a tip end of a transparent glass tube was irradiated with light and acoustic waves were received. Received signals were used to calculate a voxel value in the same position as the very-small sound source. Such an operation was repeated in various positions to experimentally obtain spatial sensitivity distribution data. The spatial sensitivity distribution data was stored in the memory 19c of the signal processing unit 20. Next, the phantom is irradiated with light as in Example 1. Obtained digital data was transferred to the workstation (WS) as the signal processing unit 20 and stored in the WS. Then, the first data exhibiting the absorption coefficient distribution was derived as in Example 1 and corrected using the experimentally obtained spatial sensitivity distribution data. As a result, second data exhibiting substantially the same absorption coefficient distribution as in the case of FIG. 4C was able to be derived.

As described above, according to the present invention, even in the case where the spatial sensitivity distribution data which is derived experimentally is used, the image of the optical absorbers in the inner portion of the subject may be quantitatively displayed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-101886, filed Apr. 27, 2010, and 2011-050008, filed Mar. 8, 2011 which are hereby incorporated by reference herein in their entirety.

What is claimed is:

1. A subject information obtaining apparatus for obtaining information about a subject comprising:
   an acoustic wave detector for detecting an acoustic wave to obtain a signal, the acoustic wave being generated from the subject when irradiated with light;
   a processor programmed with at least first and second deriving units; and
   a memory configured to store spatial sensitivity distribution data that represents fluctuations in measurement sensitivities of the subject information obtaining apparatus for respective locations in the subject,
   wherein the first data deriving unit derives first data exhibiting an optical characteristic distribution of the subject based on the signal obtained by the acoustic wave detector, and
   wherein the second data deriving unit derives second data by correcting the first data with the spatial sensitivity distribution data stored in the memory.

2. The subject information obtaining apparatus according to claim 1, wherein the processor is further programmed with a calculation unit for calculating the spatial sensitivity distribution data.

3. The subject information obtaining apparatus according to claim 2, wherein the calculation unit is configured to:
   assume a hypothetical sound source for each voxel of multiple voxels corresponding to divided portions of the subject;
   for each voxel, calculate a signal to be detected by the acoustic wave detector if the hypothetical sound source in the voxel generates an acoustic wave; and
   for each voxel, calculate a spatial sensitivity based on the calculated signal for the voxel.

4. The subject information obtaining apparatus according to claim 2, wherein the calculation unit is configured to calculate a spatial sensitivity distribution in the subject, the subject being assumed to be divided into portions corresponding to multiple voxels, based on a signal obtained by the acoustic wave detector when the acoustic wave detector detects, for each voxel of the multiple voxels, an acoustic wave generated by a sound source in the voxel.

5. The subject information obtaining apparatus according to claim 1, wherein the second data deriving unit is configured to derive the second data by dividing the first data by the spatial sensitivity distribution data.

6. The subject information obtaining apparatus according to claim 1, wherein the second data deriving unit is configured to derive the second data by multiplying the first data by the spatial sensitivity distribution data.

7. The subject information obtaining apparatus according to claim 1,
   wherein the memory is configured to store the spatial sensitivity distribution data that represents fluctuations in measurement sensitivities of the subject information obtaining apparatus and measurement sensitivities resulting from a structural or physical property of the subject for respective locations in the subject, and
   wherein the second data deriving unit is configured to derive the second data by correcting the first data with the spatial sensitivity distribution data that represents fluctuations in measurement sensitivities of the subject information obtaining apparatus and measurement sensitivities resulting from a structural or physical property of the subject for respective locations in the subject.

8. A subject information obtaining method for obtaining information about a subject using a subject information obtaining apparatus comprising the steps of:
   irradiating a subject with light;
   detecting an acoustic wave generated from the subject irradiated with the light to obtain a signal;
   deriving first data exhibiting an optical characteristic distribution of the subject based on the signal obtained in the detecting step; and
   deriving second data by correcting the first data with spatial sensitivity distribution data that represents fluctuations in measurement sensitivities of the subject information obtaining apparatus for respective locations in the subject.

9. The subject information obtaining method according to claim 8, further comprising a step of calculating the spatial sensitivity distribution data specific to the subject information obtaining apparatus.

10. A subject information obtaining apparatus for obtaining information about a subject comprising:
    an acoustic wave detector for obtaining a signal by detecting an acoustic wave generated from the subject when irradiated with light;
    a memory configured to store spatial sensitivity distribution data that represents fluctuations in measurement sensitivities of the subject information obtaining apparatus for respective locations in the subject;
    a first data deriving unit configured to derive first data exhibiting an optical characteristic distribution of the subject based on the signal obtained by the acoustic wave detector; and
    a second data deriving unit configured to derive second data by correcting the first data with the spatial sensitivity distribution data stored in the memory.

11. The subject information obtaining apparatus according to claim 10, further comprising a calculation unit for calculating the spatial sensitivity distribution data.

12. The subject information obtaining apparatus according to claim 11, wherein the calculation unit is configured to:

assume a hypothetical sound source for each voxel of multiple voxels corresponding to divided portions of the subject;

for each voxel, calculate a signal to be detected by the acoustic wave detector if the hypothetical sound source in the voxel generates an acoustic wave; and for each voxel, calculate a spatial sensitivity based on the calculated signal for the voxel.

13. The subject information obtaining apparatus according to claim 11, wherein the calculation unit is configured to calculate a spatial sensitivity distribution in the subject, the subject being assumed to be divided into portions corresponding to multiple voxels, based on a signal obtained by the acoustic wave detector when the acoustic wave detector detects, for each voxel of the multiple voxels, an acoustic wave generated by a sound source in the voxel.

14. The subject information obtaining apparatus according to claim 10, wherein the second data deriving unit is configured to derive the second data by dividing the first data by the spatial sensitivity distribution data.

15. The subject information obtaining apparatus according to claim 10, wherein the second data deriving unit is configured to derive the second data by multiplying the first data by the spatial sensitivity distribution data.

16. The subject information obtaining apparatus according to claim 10, wherein the memory is configured to store the spatial sensitivity distribution data that represents fluctuations in measurement sensitivities of the subject information obtaining apparatus and measurement sensitivities resulting from a structural or physical property of the subject for respective locations in the subject, and wherein the second data deriving unit is configured to derive the second data by correcting the first data with the spatial sensitivity distribution data that represents fluctuations in measurement sensitivities of the subject information obtaining apparatus and measurement sensitivities resulting from a structural or physical property of the subject for respective locations in the subject.

17. A subject information obtaining method for obtaining information about a subject using a signal obtained by detecting an acoustic wave generated from the subject when irradiated with light comprising the steps of:

deriving first data exhibiting an optical characteristic distribution of the subject based on the signal; and deriving second data by correcting the first data with spatial sensitivity distribution data that represents fluctuations in measurement sensitivities of the subject information obtaining apparatus for respective locations in the subject.

18. The subject information obtaining method according to claim 17, wherein, in the step of deriving the second data, the second data is derived by dividing the first data by the spatial sensitivity distribution data.

19. The subject information obtaining method according to claim 17, wherein, in the step of deriving the second data, the second data is derived by multiplying the first data by the spatial sensitivity distribution data.

20. The subject information obtaining method according to claim 17, wherein, in the step of deriving the second data, the second data is derived by correcting the first data with the spatial sensitivity distribution data that represents fluctuations in measurement sensitivities of the subject information obtaining apparatus and measurement sensitivities resulting from a structural or physical property of the subject for respective locations in the subject.

* * * * *